(12) United States Patent
Hart

(10) Patent No.: US 6,289,896 B1
(45) Date of Patent: Sep. 18, 2001

(54) CARDIAC TELEMETRY PROTECTIVE POUCH

(76) Inventor: Glennah D. Hart, P.O. Box 4565, Columbia, SC (US) 29240

( * ) Notice: Subject to any disclaimer, the term of this patent is extended or adjusted under 35 U.S.C. 154(b) by 0 days.

(21) Appl. No.: 09/470,756

(22) Filed: Dec. 23, 1999

(51) Int. Cl.$^7$ ................................................. A61B 19/02
(52) U.S. Cl. ................................ 128/897; 128/DIG. 24; 128/903; 24/385; 24/409; 206/701; 206/438; 150/154; 383/41; 383/63; 600/386
(58) Field of Search ...................... 128/90.3, 904, 128/917, DIG. 24, 897; 150/165, 154, 128; 24/3.1, 3.7, 30.5 L, 381, 385, 399, 403, 409, 411, 415; 383/41, 61, 63, 66, 79; 206/701, 702, 438; 600/509, 386, 390; 607/149

(56) References Cited

U.S. PATENT DOCUMENTS

| | | |
|---|---|---|
| D. 360,414 | 7/1995 | Wong . |
| 2,244,871 | 6/1941 | Guinburg . |
| 4,043,326 | 8/1977 | Little et al. . |
| 4,069,955 * | 1/1978 | Noyes ........................ 224/5 |
| 4,411,267 * | 10/1983 | Heyman ..................... 128/385 |
| 4,773,427 * | 9/1988 | Inoue et al. ................. 128/696 |
| 4,911,151 | 3/1990 | Rankin et al. . |
| 4,979,702 * | 12/1990 | Franklin ...................... 244/129 |
| 5,063,919 | 11/1991 | Silverberg . |
| 5,342,286 | 8/1994 | Kelly et al. . |
| 5,368,500 * | 11/1994 | Dedering .................... 439/367 |
| 5,392,973 * | 2/1995 | Benson ....................... 224/208 |
| 5,524,802 * | 6/1996 | Benson et al. ............... 224/194 |
| 5,694,940 * | 12/1997 | Unger et al. ................ 128/696 |
| 5,718,104 * | 2/1998 | Kennedy ..................... 53/491 |
| 6,048,640 * | 4/2000 | Walters et al. .............. 429/136 |
| 6,053,635 * | 4/2000 | Anderson et al. ............ 383/10 |
| 6,082,535 * | 7/2000 | Mitvchell .................... 206/320 |
| 6,085,695 * | 7/2000 | Miller et al. ................ 119/795 |
| 6,099,934 * | 8/2000 | Held .......................... 428/100 |
| 6,132,367 * | 10/2000 | Adair ......................... 600/101 |
| 6,224,258 * | 5/2001 | Dodson ....................... 383/9 |

* cited by examiner

Primary Examiner—Kennedy Schaetzle

(57) ABSTRACT

A cardiac telemetry protective pouch for providing a water resilient protective pouch for containing the telemetry electronics employed for monitoring and transmitting cardiac status information about a patient. The cardiac telemetry protective pouch includes a protective pouch comprising a pair of side panels each having a perimeter. A portion of the perimeter of a first one of the side panels is releasably coupled to a corresponding portion of the perimeter of a second one of the side panels to form a closable opening on the pouch. A remainder portion of the perimeter of the first side panel is inseparably coupled to the perimeter of the second side panel to define an interior and form a water tight seal between the side panels at the remainder portion. An interlocking closure comprises a first interlocking structure on the first side panel and a second interlocking structure on the second side panel. The first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structure are interlocked with the second interlocking structure in snug relationship with the lead wire.

8 Claims, 2 Drawing Sheets

CARDIAC TELEMETRY PROTECTIVE POUCH

BACKGROUND OF THE INVENTION

1. Field of the Invention

The present invention relates to protective coverings for electronic devices and more particularly pertains to a new cardiac telemetry protective pouch for providing a water resilient protective pouch for containing the telemetry electronics employed for monitoring and transmitting cardiac status information about a patient.

2. Description of the Prior Art

The use of protective coverings for electronic devices is known in the prior art. More specifically, protective coverings for electronic devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,063,919; U.S. Pat. No. 5,342,286; U.S. Pat. No. Des. 360,414; U.S. Pat. No. 4,911,151; U.S. Pat. No. 4,043,326; and U.S. Pat. No. 2,244,871.

While these devices fulfill their respective, particular objectives and requirements, the aforementioned patents do not disclose a new cardiac telemetry protective pouch. The inventive device includes a protective pouch for receiving the telemetry device of the cardiac telemetry monitoring apparatus. The protective pouch comprises a pair of side panels each having a perimeter. A portion of the perimeter of a first one of the side panels is releasably coupled to a corresponding portion of the perimeter of a second one of the side panels to form a closable opening on the pouch. A remainder portion of the perimeter of the first side panel is inseparably coupled to the perimeter of the second side panel to define an interior and form a water tight seal between the side panels at the remainder portion. An interlocking closure is for releasably joining the side panels at the closable opening. The interlocking closure comprises a first interlocking structure on the first side panel and a second interlocking structure on the second side panel. The first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structure are interlocked with the second interlocking structure in snug relationship with the lead wire.

In these respects, the cardiac telemetry protective pouch according to the present invention substantially departs from the conventional concepts and designs of the prior art, and in so doing provides an apparatus primarily developed for the purpose of providing a water resilient protective pouch for containing the telemetry electronics employed for monitoring and transmitting cardiac status information about a patient.

SUMMARY OF THE INVENTION

In view of the foregoing disadvantages inherent in the known types of protective coverings for electronic devices now present in the prior art, the present invention provides a new cardiac telemetry protective pouch construction wherein the same can be utilized for providing a water resilient protective pouch for containing the telemetry electronics employed for monitoring and transmitting cardiac status information about a patient.

The general purpose of the present invention, which will be described subsequently in greater detail, is to provide a new cardiac telemetry protective pouch apparatus and method which has many of the advantages of the protective coverings for electronic devices mentioned heretofore and many novel features that result in a new cardiac telemetry protective pouch which is not anticipated, rendered obvious, suggested, or even implied by any of the prior art protective coverings for electronic devices, either alone or in any combination thereof.

To attain this, the present invention generally comprises a protective pouch for receiving the telemetry device of the cardiac telemetry monitoring apparatus. The protective pouch comprises a pair of side panels each having a perimeter. A portion of the perimeter of a first one of the side panels is releasably coupled to a corresponding portion of the perimeter of a second one of the side panels to form a closable opening on the pouch. A remainder portion of the perimeter of the first side panel is inseparably coupled to the perimeter of the second side panel to define an interior and form a water tight seal between the side panels at the remainder portion. An interlocking closure is for releasably joining the side panels at the closable opening. The interlocking closure comprises a first interlocking structure on the first side panel and a second interlocking structure on the second side panel. The first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structure are interlocked with the second interlocking structure in snug relationship with the lead wire.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new cardiac telemetry protective pouch apparatus and method which has many of the advantages of the protective coverings for electronic devices mentioned heretofore and many novel features that result in a new cardiac telemetry protective pouch which is not anticipated, rendered obvious, suggested, or even implied by any of the prior art protective coverings for electronic devices, either alone or in any combination thereof.

It is another object of the present invention to provide a new cardiac telemetry protective pouch which may be easily and efficiently manufactured and marketed.

It is a further object of the present invention to provide a new cardiac telemetry protective pouch which is of a durable and reliable construction.

An even further object of the present invention is to provide a new cardiac telemetry protective pouch which is susceptible of a low cost of manufacture with regard to both materials and labor, and which accordingly is then susceptible of low prices of sale to the consuming public, thereby making such cardiac telemetry protective pouch economically available to the buying public.

Still yet another object of the present invention is to provide a new cardiac telemetry protective pouch which provides in the apparatuses and methods of the prior art some of the advantages thereof, while simultaneously overcoming some of the disadvantages normally associated therewith.

Still another object of the present invention is to provide a new cardiac telemetry protective pouch for providing a water resilient protective pouch for containing the telemetry electronics emplyed for monitoring and transmitting cardiac status information about a patient.

Yet another object of the present invention is to provide a new cardiac telemetry protective pouch which includes a protective pouch for receiving the telemetry device of the cardiac telemetry monitoring apparatus. The protective pouch comprises a pair of side panels each having a perimeter. A portion of the perimeter of a first one of the side panels is releasably coupled to a corresponding portion of the perimeter of a second one of the side panels to form a closable opening on the pouch. A remainder portion of the perimeter of the first side panel is inseparably coupled to the perimeter of the second side panel to define an interior and form a water tight seal between the side panels at the remainder portion. An interlocking closure is for releasably joining the side panels at the closable opening. The interlocking closure comprises a first interlocking structure on the first side panel and a second interlocking structure on the second side panel. The first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structure are interlocked with the second interlocking structure in snug relationship with the lead wire.

Still yet another object of the present invention is to provide a new cardiac telemetry protective pouch that provides a substantially watertight pouch in which sensitive telemetry electronics may be held during patient activities such, for example, during patient showers.

Even still another object of the present invention is to provide a new cardiac telemetry protective pouch that provides a pouch that shields the more water sensitive portion of the telemetry equipment while leaving the less water sensitive portions exposed.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
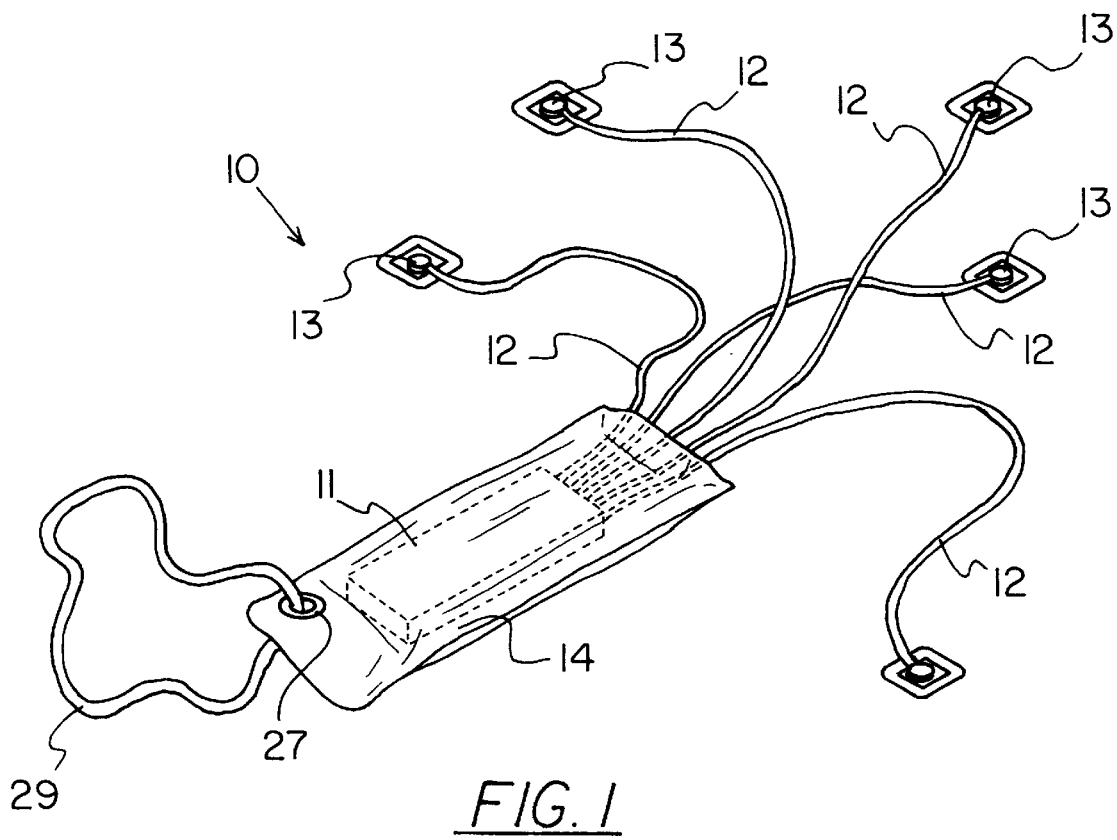
FIG. 1 is a perspective view of a new cardiac telemetry protective pouch according to the present invention.
Figure 2:
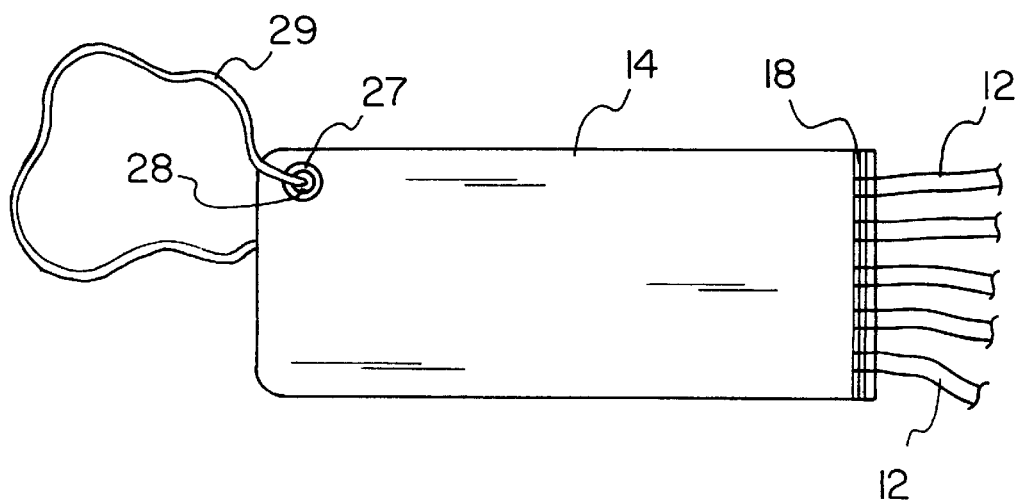
FIG. 2 is a top plan view of the present invention.
Figure 3:
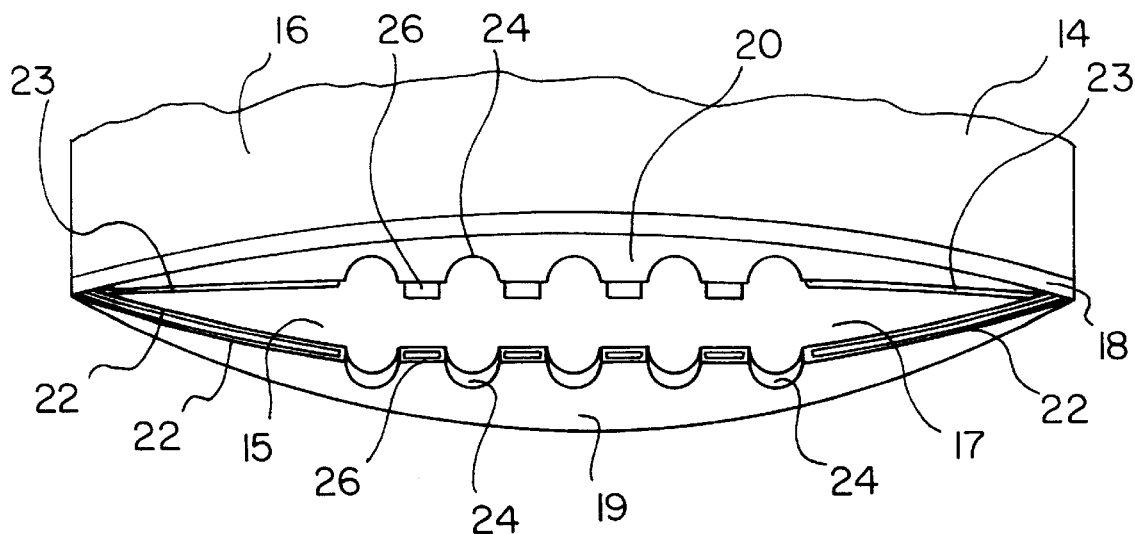
FIG. 3 is an enlarged perspective view of the interlocking closure of the present invention.
Figure 4:
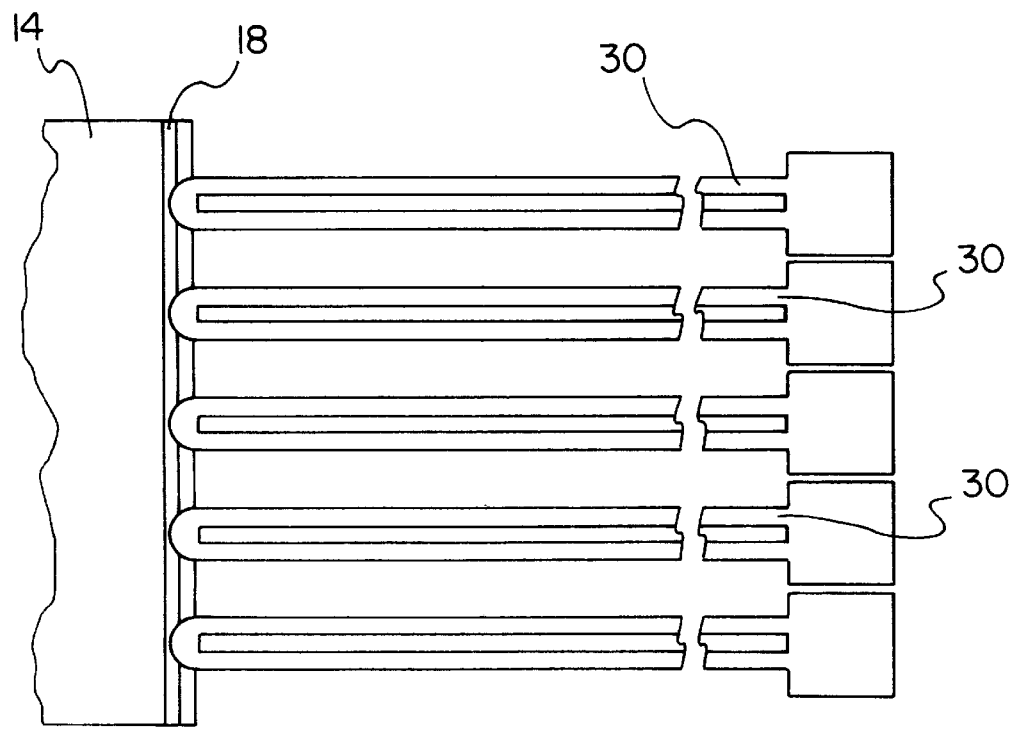
FIG. 4 is a top view of the lead wire covers of the present invention.

With reference now to the drawings, and in particular to FIGS. 1 through 4 thereof, a new cardiac telemetry protective pouch embodying the principles and concepts of the present invention and generally designated by the reference numeral 10 will be described.

As best illustrated in FIGS. 1 through 4, the cardiac telemetry protective pouch 10 generally comprises a cardiac telemetry monitoring apparatus for monitoring and transmitting information about the cardiac status of a patient. The cardiac telemetry monitoring apparatus comprises a telemetry device 11, a housing, and a battery compartment in the housing. A plurality of lead wires 12 are removably connected to the telemetry device, wherein the plurality of lead wires comprises five lead wires. A plurality of electrodes 13 each connected to one of the plurality of lead wires.

A protective pouch 14 for receiving the telemetry device of the cardiac telemetry monitoring apparatus. The protective pouch comprises a pair of side panels each having a perimeter. A portion of the perimeter of a first one of the side panels 15 is releasably coupled to a corresponding portion of the perimeter of a second one of the side panels 16 to form a closable opening on the pouch. A remainder portion of the perimeter of the first side panel is inseparably coupled to the perimeter of the second side panel to define an interior 17 and form a water tight seal between the side panels at the remainder portion.

An interlocking closure 18 is for releasably joining the side panels at the closable opening. The interlocking closure comprises a first interlocking structure 19 on the first side panel and a second interlocking structure 20 on the second side panel. The first interlocking structure comprises a pair of protruding lips 22 extending in a spaced parallel relationship along the portion of the first side panel forming the closable opening. The second interlocking structure comprises at least one protruding lip 23 extending along the portion of the second side panel forming the closable opening and is releasably insertable between and interlockable with the pair of protruding lips of the first side panel. The first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structures are interlocked with the second interlocking structures in snug relationship with the lead wire.

A plurality of gaps 24 are formed in the first and second interlocking structures and adjacent gaps are separated by segments of the first and second interlocking structures. The interlocking closure comprises at least five holes in the interlocking closure for permitting at least five leads to extend out of the interior. A lip segment 26 on each of the first and second interlocking structures extends between adjacent gaps in the protruding lips of the first and second interlocking structures. One of the lip segments of the first interlocking structure is interlockable with one of the lip segments of the second interlocking structure.

A grommet 27 extends through the first and second side panels. The grommet is located on the pouch at a location spaced from the closable opening such that when the pouch is suspended from the grommet, the pouch hangs in an inverted position with the closable opening directed downwardly to shed water away from the closable opening. The grommet comprises an aperture 28 therethrough. The grommet is substantially circular. A tether strap 29 is for supporting the pouch in a shower stall. The tether strap comprises an endless loop extending through the aperture of the grommet.

In an embodiment a plurality of lead wire covers 30 may be provided which encompass the lead wires therein and protect the lead wires from contact with water. The lead wire covers are formed such that the lead wire covers fit in the gaps formed in the first and second interlocking structures such that a water resistant seal is formed between the lead wire covers and the interlocking structures when the interlocking structures are sealed.

In use, a user would place the telemetry apparatus within the pouch and place the lead wire covers over the lead wires of the telemetry unit. The closable end of the pouch would then be sealed with the lead wires protruding outwardly from the pouch The lead wires could then be placed upon a patient and the tether strap slung over the shoulder to aid in the carrying of the telemetry unit.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cardiac telemetry protective system for protective carrying of monitoring and transmitting cardiac information of a patient, the cardiac telemetry protective system comprising:

a protective pouch for receiving the telemetry device of the cardiac telemetry monitoring apparatus, the protective pouch comprising:

a pair of side panels each having a perimeter, a portion of the perimeter of a first one of the side panels being releasably coupled to a corresponding portion of the perimeter of a second one of the side panels to form a closable opening on the pouch, a remainder portion of the perimeter of the first side panel being inseparably coupled to the perimeter of the second side panel to define an interior and form a water tight seal between the side panels at the remainder portion; and an interlocking closure for releasably joining the side panels at the closable opening, the interlocking closure comprising a first interlocking structure on the first side panel and a second interlocking structure on the second side panel, wherein the first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structure is interlocked with the second interlocking structure in snug relationship with the lead wire.

2. The cardiac telemetry protective system as set forth in claim 1 wherein the first interlocking structure comprises a pair of protruding lips extending in a spaced parallel relationship along the portion of the first side panel forming the closable opening, the second interlocking structure comprising at least one protruding lip extending along the portion of the second side panel forming the closable opening and being releasably insertable between and interlockable with the pair of protruding lips of the first side panel.

3. The cardiac telemetry protective system as set forth in claim 1 wherein a plurality of gaps are formed in the first and second interlocking structures and adjacent gaps are separated by segments of the first and second interlocking structures.

4. The cardiac telemetry protective system as set forth in claim 3 wherein the interlocking closure has at least five said holes closure for permitting at least five leads to extend out of the interior.

5. The cardiac telemetry protective system as set forth in claim 3 wherein a lip segment on each of the first and second interlocking structures extends between adjacent gaps in the protruding lips of the first and second interlocking structures, one of the lip segments of the first interlocking structure being interlockable with one of the lip segments of the second interlocking structure.

6. The cardiac telemetry protective system as set forth in claim 1 further comprises a grommet extending through the first and second side panels, the grommet being located on the pouch at a location spaced from the closable opening such that when the pouch is suspended from the grommet, the pouch hangs in an inverted position with the closable opening directed downwardly to shed water away from the closable opening, the grommet having an aperture therethrough, the grommet being substantially circular.

7. The cardiac telemetry protective system as set forth in claim 6 further comprises a tether strap for supporting the pouch in a shower stall, the tether strap comprising an endless loop extending through the aperture of the grommet.

8. A cardiac telemetry protective system for protective carrying of monitoring and transmitting cardiac information of a patient, the cardiac telemetry protective system comprising:

a cardiac telemetry monitoring apparatus for monitoring and transmitting information about the cardiac status of a patient, the cardiac telemetry monitoring apparatus comprising:
     a telemetry device, a housing, a battery compartment in the housing;
     a plurality of lead wires removably connected to the telemetry device, wherein the plurality of lead wires comprises five lead wires;
     a plurality of electrodes, each of the electrodes being connected to one of the plurality of lead wires;

a protective pouch for receiving the telemetry device of the cardiac telemetry monitoring apparatus, the protective pouch comprising:
     a pair of side panels each having a perimeter, a portion of the perimeter of a first one of the side panels being releasably coupled to a corresponding portion of the perimeter of a second one of the side panels to form a closable opening on the pouch, a remainder portion of the perimeter of the first side panel being inseparably coupled to the perimeter of the second side panel to define an interior and form a water tight seal between the side panels at the remainder portion;
     an interlocking closure for releasably joining the side panels at the closable opening, the interlocking closure comprising a first interlocking structure on the first side panel and a second interlocking structure on the second side panel, the first interlocking structure comprising a pair of protruding lips extending in a spaced parallel relationship along the portion of the first side panel forming the closable opening, the second interlocking structure comprising at least one protruding lip extending along the portion of the second side panel forming the closable opening and being releasably insertable between and interlockable with the pair of protruding lips of the first side panel, wherein the first interlocking structure of the first side panel and second interlocking structure of the second panel each have at least one gap therein at alignable locations of the closable opening such that a hole is formed between the first and second side panels when the first and second interlocking structures of the side panels are interlocked together for permitting passage of a lead wire through the interlocking closure when the first interlocking structure is interlocked with the second interlocking structure in snug relationship with the lead wire, wherein a plurality of gaps are formed in the first and second interlocking structures and adjacent gaps are separated by segments of the first and second interlocking structures, the interlocking closure having at least five holes in the interlocking closure for permitting at least five leads to extend out of the interior, a lip segment on each of the first and second interlocking structures extending between adjacent gaps in the protruding lips of the first and second interlocking structures, one of the lip segments of the first interlocking structure being interlockable with one of the lip segments of the second interlocking structure;

a grommet extending through the first and second side panels, the grommet being located on the pouch at a location spaced from the closable opening such that when the pouch is suspended from the grommet, the pouch hangs in an inverted position with the closable opening directed downwardly to shed water away from the closable opening, the grommet having an aperture therethrough, the grommet being substantially circular; and a tether strap for supporting the pouch in a shower stall, the tether strap comprising an endless loop extending through the aperture of the grommet.

* * * * *